United States Patent [19]
Fleck et al.

[11] 4,152,438
[45] May 1, 1979

[54] PHENOXYALKYLAMINEPYRIDYLETHERS

[75] Inventors: Wolfgang Fleck, Hamburg; Rudolf Petersen, Wohltorf; Heinrich Bahrmann, Ellerau, all of Fed. Rep. of Germany

[73] Assignee: Beiersdorf Aktiengesellschaft, Hamburg, Fed. Rep. of Germany

[21] Appl. No.: 834,463

[22] Filed: Sep. 19, 1977

Related U.S. Application Data

[63] Continuation of Ser. No. 702,639, Jul. 6, 1978, abandoned.

[30] Foreign Application Priority Data

Jul. 10, 1975 [DE] Fed. Rep. of Germany ....... 2530768

[51] Int. Cl.² ................. C07D 213/36; C07D 213/55; C07D 213/57; A61K 31/44
[52] U.S. Cl. ..................................... 424/263; 546/288; 546/296; 546/297; 546/298; 546/300; 424/266
[58] Field of Search .......... 260/294.9, 296 AE, 295 S, 260/570.7 R, 295 R, 295.5 R; 424/263, 330; 546/288, 296, 297, 298, 300

[56] References Cited

U.S. PATENT DOCUMENTS

| 3,154,581 | 10/1964 | Dice | 260/570.7 R |
| 3,960,878 | 6/1976 | Petersen et al. | 260/296 AE |
| 3,993,780 | 11/1976 | Nakao et al. | 260/570.7 R |

Primary Examiner—Alan L. Rotman
Attorney, Agent, or Firm—Bierman & Bierman

[57] ABSTRACT

Phenoxyalkylaminepyridyl ethers of the formula

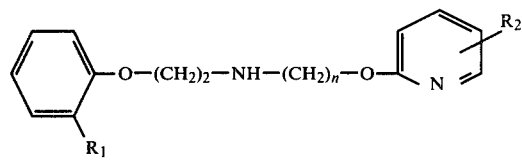

wherein $R_1$ is methyl, methoxy, or chlorine; $R_2$ is hydrogen, methyl, alkoxy containing 1 to 4 carbon atoms, nitro, amino, halogen, cyano, or a residue of the formula

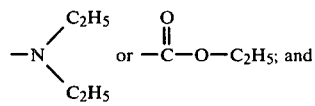

n is 2 or 3, and their physiologically acceptable acid addition salts. These compounds are useful for lowering blood pressure.

8 Claims, No Drawings

PHENOXYALKYLAMINEPYRIDYLETHERS

This application is a continuation of Ser. No. 702,639, filed July 6, 1978, which claims priority of German Application P 25 30 768.0, filed July 10, 1976 now abandoned.

The present invention is directed to an improved class of pharmaceutical compounds; more particularly, to certain ethers, and salts thereof, useful in reducing blood pressure.

The active compounds of the present invention are phenoxyalkylaminepyridyl ethers of the formula

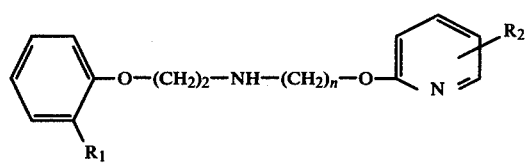
(I)

wherein $R_1$ is methyl, methoxy, or chlorine; $R_2$ is hydrogen, methyl, alkoxy, containing 1 to 4 carbon atoms, nitro, amino, halogen, cyano, or a residue of the formula

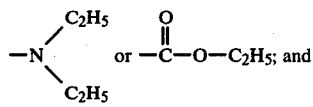

n is 2 or 3 and physiologically acceptable acid addition salts thereof.

The compounds falling within the foregoing class have valuable pharmacological properties. When given in single doses of 10 to 50 mg/kg, the blood pressure was reduced by approximately 10 to 20 percent of its initial value in most cases. In some cases, the maximum reduction was deferred to up to 24 hours after administration.

The ethers of the present invention are preferably used in the form of easily crystallizable acid addition salts, such as hydrochlorides, oxalates, maleates, as well as salts of sulfuric acid, phosphoric acid, toluene sulfonic acid, citric acid and malic acid. The first three are preferred, but all physiologically acceptable acids are suitable.

The active compounds of the present invention may be mixed with suitable carriers, diluents, and/or adjuvants. They may be in the form of solutions, suspensions, emulsions, pills, tablets, dragées, etc. The compounds may be administered in any normal manner, injections and especially per os being preferred.

The compounds of the present invention are prepared by reaction of an amino alcohol of the formula

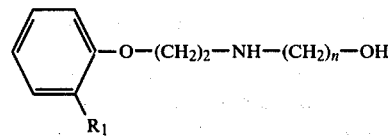
(II)

or of an alkali salt thereof, with a substituted pyridine of the formula

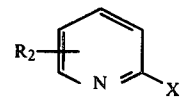
(III)

wherein X represents a halogen atom, preferably chlorine, bromine, or iodine.

The foregoing reaction is carried out preferably in an inert organic solvent, refluxing for several hours. The molecular ratio of the reactants is preferably 1 to 1. The reaction time varies, depending upon the reactants themselves, but is generally from about 3 to 8 hours. While the solvents used are not critical, benzene, toluene, xylene and the like have been found suitable. Toluene and xylene are preferred. The isolation of the reaction products may be carried out in the usual manner without any problems.

Optionally, easily crystallizable acid addition salts may be prepared from the bases, which often precipitate as oily products. The addition salts are prepared in the usual manner by dissolving the base in an organic solvent and precipitating the desired salt with acid. The crude precipitated salt may be further purified by recrystallization. The preferred acids are hydrochloric, oxalic, and maleic. Also suitable are sulfuric, phosphoric, toluene sulfonic, citric, and malic acids. In general, pharmaceutically acceptable acids are suitable for forming the acid addition salts. If desired, the purified salts can be reconverted into the free base by reaction with a basic substance in the usual manner.

The starting amino alcohols of Formula II may be prepared by reacting the corresponding phenoxyalkylbromides (or chlorides) with amino ethanol or amino propanol (see I. F. Kerwin, G. C. Hall, et al.: "Journal of the American Chemical Society" 73 [1951]p. 4162). The substituted pyridines (Formula III) are known compounds which are described in the chemical literature.

The following examples are intended to further illustrate the present invention.

EXAMPLE 1

N-[2-Pyridyloxy-ethyl(2)]-o-methoxy-phenoxyethylamine oxalate.

N-[o-methoxy-phenoxyethyl]-amino-ethan-2-ol in an amount of 21.1 grams (0.1 mol) was refluxed in 100 ml of xylene with 2.3 grams (0.1 mol) of sodium for three hours. The reaction mixture was then cooled to approximately 40° C. and 15.8 grams (0.1 mol) of 2-bromo pyridine was added in small portions. Thereafter the reaction mixture was further refluxed for an additional four hours.

The reaction mixture was cooled to room temperature and then shaken with 1 N-hydrochloric acid. The aqueous phase was separated and made alkaline with 2N-caustic soda (sodium hydroxide). Thereafter, the alkaline phase was extracted three times using 100 ml of ether each time. The ether extracts were combined and the resultant ether phase was dried with anhydrous sodium sulfate and acidified with oxalic acid in ether solution. The desired product was crystallized from the reaction mixture and, thereafter, recrystallized from water. The purified compound had a melting point of 205° C. and was recovered in a yield of 29%.

Analysis for $C_{16}H_{20}N_2O_3$.oxalate

| Calculated: | Found: |
|---|---|
| C = 57,30 % | C = 57,51 % |
| H = 5,89 % | H = 5,78 % |
| N = 7,44 % | N = 7,22 % |

EXAMPLE 2

N-[6-Ethoxy-2-pyridyloxy-ethyl (2)]-o-methoxy-phenoxyethylamine oxalate

N-[o-methoxy-phenoxyethyl]-amino ethan-2-ol in an amount of 10.55 grams (0.05 mol) and 1.15 grams of sodium (0.05 mol) were refluxed in 50 ml of anhydrous xylene for three hours. The reaction mixture was permitted to cool to room temperature and 10.1 grams (0.05 mol) of 6-ethoxy-2-bromo-pyridine was added. The reaction mixture was refluxed for an additional four hours.

After cooling to room temperature, the reaction mixture was shaken with 1N-hydrochloric acid. The aqueous phase was separated and made alkaline with 2N-caustic soda (sodium hydroxide). This phase was then extracted three times with ether, the extracts were combined, and the ether phase was dried with anhydrous sodium sulfate. It was then acidified with oxalic acid in ether solution. The desired compound was crystallized from the reaction mixture and purified by recrystallization from a mixture of equal amounts of water and methanol. The melting point of the reaction product was 207° C. and the yield was 38%.

Analysis for $C_{18}H_{24}N_2O_4$.oxalate

| Calculated: | Found: |
|---|---|
| C = 56,90 % | C = 56,59 % |
| H = 6,16 % | H = 6,15 % |
| N = 6,63 % | N = 6,34 % |

The following new ethers can be produced from their corresponding amino alcohols (or alkali salts thereof) by reaction with corresponding substituted pyridines. The reactions are carried out in a manner analagous to those of the foregoing examples. Following each compound is its melting point in degrees centigrade.

| | | |
|---|---|---|
| 3. | N-[2-Pyridyloxy-propyl (3)]-o-methoxy-phenoxyethylamine-oxalate semihydrate | 171° |
| 4. | N-[4-Methyl-2-pyridyloxy-ethyl (2)]-o-methoxy-phenoxyethylamine oxalate | 205° |
| 5. | N-[3-Methyl-2-pyridyloxy-ethyl (2)]-o-methoxy-phenoxyethylamine oxalate | 198° |
| 6. | N-[6-Methyl-2-pyridyloxy-ethyl (2)]-o-methoxy-phenoxyethylamine oxalate semihydrate | 197° |
| 7. | N-[6-Bromo-2-pyridyloxy-ethyl (2)]-o-methoxy-phenoxyethylamine hydrochloride semihydrate | 128° |
| 8. | N-[6-Methoxy-2-pyridyloxy-ethyl (2)]-o-methoxy-phenoxyethylamine oxalate semihydrate | 205° |
| 9. | N-[3-Nitro-2-pyridyloxy-ethyl (2)]-o-methoxy-phenoxyethylamine oxalate | 186° |
| 10. | N-[5-Nitro-2-pyridyloxy-ethyl (2)]-o-methoxy-phenoxyethylamine hydrochloride | 148° |
| 11. | N-[3-Amino-2-pyridyloxy-ethyl (2)]-o-methoxy-phenoxyethylamine dihydrochloride hydrate (obtained by reduction of the corresponding nitro compound with hydrogen of 100 at pressure in ethanol solution by using Raney nickel as catalyst) | 148° |
| 12. | N-[2-Pyridyloxy-ethyl (2)]-o-methyl-phenoxy-ethylamine oxalate | 198° |
| 13. | N-[6-Diethylamino -2-pyridyloxy-ethyl (2)]-o-methoxy-phenoxyethylamine oxalate semihydrate | 184° |
| 14. | N-[5-Carbethoxy-2-pyridyloxy-ethyl (2)]-o-methoxy-phenoxyethylamine oxalate hydrate | 183° |
| 15. | N-[3-Cyano-2-pyridyloxy-ethyl (2)]-o-methoxy-phenoxyethylamine oxalate | 185° |
| 16. | N-[3-Cyano-2-pyridyloxy-ethyl (2)]-o-methyl-phenoxyethylamine-hydrochloride | 186° |
| 17. | N-[2-Pyridyloxy-ethyl (2)]-o-chloro-phenoxy-ethylamine oxalate | 194° |

While only a limited number of embodiments of the present have been specifically described, it is, nonetheless, to be broadly construed and not to be limited except by the character of the claims appended hereto.

We claim:

1. Phenoxyalkylaminepyridylethers of the formula

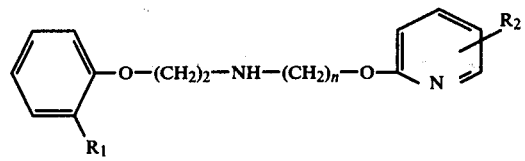

wherein $R_1$ is a methyl, methoxy, or chlorine;

$R_2$ is hydrogen, methyl, alkoxy containing 1 to 4 carbon atoms; nitro, amino, halogen, cyano, or a residue of the formula

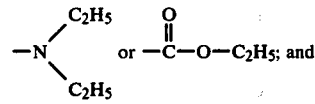

n is 2 or 3 and/or their physiologically acceptable acid addition salts.

2. The compound of claim 1 wherein $R_1$ is methoxy, $R_2$ is 3-methyl, and n equals 2.

3. A compound according to claim 1 wherein $R_2$ is hydrogen, methyl, alkoxy containing 1 to 4 carbon atoms; nitro, amino, halogen, cyano, or a residue of the formula:

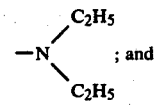

n is 2 or 3 and/or their physiologically acceptable acid addition salts.

4. A compound according to claim 3, taken from the class consisting of:

N-[2-Pyridyloxy-ethyl (2)]-o-methoxy-phenoxyethylamine oxalate;

N-[6-Ethoxy-2-pyridyloxy-ethyl (2)]-o-methoxy-phenoxyethylamine oxalate;

N-(2-Pyridyloxy-propyl (3))-o-methoxy-phenoxyethylamine-oxalate semihydrate

N-(4-Methyl-2-pyridyloxy-ethyl (2))-o-methoxy-phenoxyethylamine oxalate

N-(3-Methyl-2-pyridyloxy-ethyl (2))-o-methoxy-phenoxyethylamine oxalate

N-(6-Methyl-2-pyridyloxy-ethyl (2))-o-methoxy-phenoxyethylamine oxalate semihydrate N-(6-Bromo-2-pyridyloxy-ethyl (2))-o-methoxy-phenoxyethylamine hydrochloride semihydrate N-(6-Methoxy-2-pyridyloxy-ethyl (2))-o-methoxy-phenoxyethylamine oxalate semihydrate N-(3-Nitro-2-pyridyloxy-ethyl (2))-o-methoxy-phenoxyethylamine oxalate N-(5-Nitro-2-pyridyloxy-ethyl (2))-o-methoxy-phenoxyethylamine hydrochloride N-(3-Amino-2-pyridyloxy-ethyl (2))-o-methoxy-phenoxyethylamine dihydrochloride hydrate N-(2-Pyridyloxy-ethyl (2))-o-methyl-phenoxyethylamine oxalate N-(6-Diethylamino-2-pyridyloxy-ethyl (2))-o-methoxy-phenoxyethylamine oxalate semihydrate N-(3-Cyano-2-pyridyloxy-ethyl (2))-o-methoxy-phenoxyethylamine oxalate N-(3-Cyano-2-pyridyloxy-ethyl (2))-o-methyl-phenoxyethylamine-hydrochloride N-(2-Pyridyloxy-ethyl (2))-o-chloro-phenoxyethylamine oxalate 5. A compound according to claim 3, which is an acid addition salt.

6. An antihypertensive composition which comprises a compound of claim 3, or a physiologically acceptable acid addition salt thereof, and a pharmacologically acceptable carrier and/or diluent.

7. A pharmaceutical composition according to claim 6 wherein $R_1$ is methoxy, $R_2$ is 3-methyl, and n equals 2.

8. An antihypertensive composition comprising a pharmacologically acceptable carrier and/or diluent and a compound taken from the class consisting of:

N-(5-Nitro-2-pyridyloxy-ethyl (2))-o-methoxy-phenoxyethylamine hydrochloride

N-(3-Amino-2-pyridyloxy-ethyl (2))-o-methoxy-phenoxyethylamine dihydrochloride hydrate N-(2-Pyridyloxy-ethyl (2))-o-methyl-phenoxyethylamine oxalate N-(6-Diethylamino-2-pyridyloxy-ethyl (2))-o-methoxy-phenoxyethylamine oxalate semihydrate N-(3-Cyano-2-pyridyloxy-ethyl (2))-o-methoxy-phenoxyethylamine oxalate N-(3-Cyano-2-pyridyloxy-ethyl (2))-o-methyl-phenoxyethylamine-hydrochloride N-(2-Pyridyloxy-ethyl (2))-o-chloro-phenoxyethylamine oxalate N-(2-Pyridyloxy-propyl (3))-o-methoxy-phenoxyethylamine-oxalate semihydrate N-(4-Methyl-2-pyridyloxy-ethyl (2))-o-methoxy-phenoxyethylamine oxalate N-(3-Methyl-2-pyridyloxy-ethyl (2))-o-methoxy-phenoxyethylamine oxalate N-(6-Methyl-2-pyridyloxy-ethyl (2))-o-methoxy-phenoxyethylamine oxalate semihydrate N-(6-Bromo-2-pyridyloxy-ethyl (2))-o-methoxy-phenoxyethylamine hydrochloride semihydrate N-(6-Methoxy-2-pyridyloxy-ethyl (2))-o-methoxy-phenoxyethylamine oxalate semihydrate N-(3-Nitro-2-pyridyloxy-ethyl (2))-o-methoxy-phenoxyethylamine oxalate and physiologically acceptable acid salts thereof.

* * * * *

UNITED STATES PATENT AND TRADEMARK OFFICE
CERTIFICATE OF CORRECTION

PATENT NO. : 4,152,438
DATED : May 1, 1979
INVENTOR(S) : FLECK, et al

It is certified that error appears in the above-identified patent and that said Letters Patent are hereby corrected as shown below:

Title Page, Left Column, Number (63)  Cancel "1978"  insert -- 1976 --

Column 1, line 4, cancel "1978" insert -- 1976 --

Column 1, line 5, cancel "1976" insert -- 1975 --

Signed and Sealed this

Fourteenth Day of August 1979

[SEAL]

Attest:

Attesting Officer

LUTRELLE F. PARKER
Acting Commissioner of Patents and Trademarks